(12) United States Patent
Soker et al.

(10) Patent No.: US 7,666,393 B2
(45) Date of Patent: Feb. 23, 2010

(54) METHODS FOR ASSESSING ANTIANGIOGENIC AGENTS

(75) Inventors: Shay Soker, Greensboro, NC (US); Anthony Atala, Winston-Salem, NC (US); Gunter Schuch, Hamburg (DE)

(73) Assignee: Children's Medical Center Corporation, Boston, MA (US)

( * ) Notice: Subject to any disclaimer, the term of this patent is extended or adjusted under 35 U.S.C. 154(b) by 118 days.

(21) Appl. No.: 10/142,165

(22) Filed: May 9, 2002

(65) Prior Publication Data

US 2002/0192730 A1 Dec. 19, 2002

Related U.S. Application Data

(60) Provisional application No. 60/290,390, filed on May 11, 2001.

(51) Int. Cl.
*A61K 49/00* (2006.01)
*G01N 33/574* (2006.01)

(52) U.S. Cl. .............................. 424/9.2; 435/4; 435/7.1; 435/7.23

(58) Field of Classification Search ...................... 435/4, 435/7.24; 424/9.1
See application file for complete search history.

(56) References Cited

U.S. PATENT DOCUMENTS

2002/0051762 A1 * 5/2002 Rafii et al. ................. 424/93.1

OTHER PUBLICATIONS

Ito et al. (Cancer Research, vol. 59, pp. 5875-5877, 1999, IDS).*
Ito et al (Cancer Research, vol. 59, pp. 5875-5877, 1999, IDS).*
Takahashi et al (Nat Med, 1999, 5:434-438, IDS).*
Asahara et al (Circulation Research, 1999, 85:221-228, IDS).*
Isner et al (J Clinical Investigation, 1999, 103:1231-1236, IDS).*
Eder et al ("Recombinant Human Endostatin: Results of a Phase I Clinical Trial" Presented in Amsterdam, American Association of Cancer Research, Nov. 7, 2000, IDS).*
Ito et al (Cancer Research, vol. 59, pp. 5875-5877, 1999, IDS).*
Mancuso et al (Blood, Nov. 2000, 96(11): p. 59b, abstract #3926, IDS).*
Kas-Deleen et al (Clinical and Diagnostic laboratory Immunology, 1998, 5:622-626).*
Asahara, et al., (1999). *Circ. Res.* 85, 221-28.
Asahara, et al., (1997). *Science* 275, 964-967.
Asahara, et al., (1999). *EMBO. J.* 18 (14), 3964-72.
Battegay, E. J. (1995). *J. Mol. Med.* 73, 333-46.
Breier, et al., (1992). *Development* 114, 521-32.
Connolly, et al., (1989) *J. Biol. Chem.* 264:20017-24.
Cullinan-Bove, et al., (1993) *Endocrinology* 133:829-37.
Drake, et al., (1998). *Ann N. Y. Acad. Sci. 857*, 155-79.
Fan, et al., (1995) *Trends Pharmacol. Sci.* 16:57-66.
Ferrara, (1995) *Breast Cancer Research and Treatment* 36, 127-37.
Folkman, (1990) *J. Natl. Cancer Inst.* 82:4-6.
Folkman, (1995) *Nature Medicine* 1:27-31.
Folkman, (1995) *New England J. of Med.* 333:1757-63.
Folkman, (1995) *Mol. Med.* 1:120-22.
Folkman, (1996) *Scientific American* 275:150-54.
Folkman, (1992) *Semin. Cancer Biol.* 3:65-71.
Folkman and D'Amore, (1996) *Cell* 87:1153-55.
Frank, et al., (1995) *J. Biol. Chem.* 270:12607-13.
Jakeman, et al., (1993) *Endocrinology*, 133:848-59.
Joki, et al., (2001) *Nat. Biotechnol.* 19:35-39.
Kenyon, et al., (1996) *Invest. Ophthalmol. Vis. Sci.* 37:1625-32.
Kim, et al., (1993) *Nature* 362:841-44.
King and Brownlee, (1996) *Endocrinol. Metab. Clin. North Am.* 25:255-70.
Kolch, et al., (1995) *Breast Cancer Research and Treatment*, 36:139-55.
Nguyen, et al., (1994) *Microvasc. Res.* 47:31-40.
O'Reilly, et al., (1997) *Cell* 88:277-85.
O'Reilly, et al., (1994) *Cell* 79:315-28.
Rivard and Isner, (1998) *Mol. Med.* 4:429-40.
Senger, et al., (1993) *Cancer and Metastasis Reviews* 12:303-24.
Shi, et al., (1998) *Blood* 92:362-27.
Shweiki, et al., (1993) *J. Clin. Invest.* 91:2235-43.
Takahashi, et al., (1999) *Nat. Med.* 5:434-48.
Weidner, et al., (1991) *New England J. of Med.* 324:1-8.
Weidner, N., (1995) *Amer. J. Path.* 147:9-19.
Yancopoulos, et al., (1998) *Cell* 93:661-64.
Ito, H., et al. (1999) *Cancer Research*, 59, 5875-5877.
Asahara, T., et al. (1999) *Circ Res.*, 85, 221-228.
Asahara, T., et al. (1997) *Science*, vol. 275, 964-967.

(Continued)

*Primary Examiner*—Laura B Goddard
(74) *Attorney, Agent, or Firm*—Nixon Peabody LLP

(57) ABSTRACT

We have discovered that endothelial progenitor cells (EPC) are particularly suitable for use in a sensitive assay for antiangiogenic factors. We have found that EPC mobilization and differentiation is greatly inhibited by antiangiogenic factors as evidenced in vivo by VEGF inducing a massive mobilization of EPC into the blood circulation which effect is significantly inhibited by endostatin treatment, and, in vitro, human blood-derived EPC forming adherent colonies, which colonies, in the presence of angiogenic factors, give rise to differentiated EC, and which differentiation is disrupted and cell growth is inhibited in the presence of angiostatin and endostatin.

8 Claims, 6 Drawing Sheets

OTHER PUBLICATIONS

Isner, J.M., et al. (1999) *The Journal of Clinical Investigation*, vol. 103, No. 9, 1231-1236.

Mancuso, P. et al., "Resting and activated endothelial cells are increased in the peripheral blood of cancer patients." Blood 97(11):3658-3661, 2001.

Mancuso, P, et al., "Resting and activated endothelial cells are increased in the peripheral blood of cancer patients." Abstract, Blood 96(11):59b, 2000.

Rafii, S., "Circulating endothelial precursors: mystery, reality, and promise." J Clin Invest 105(1):17-19, 2000.

Monestiroli, S. et al., "Kinetics and Viability of Circulating Endothelial Cells As Surrogate Angiogenesis Marker in an Animal Model of Human Lymphoma." Cancer Res 61:4341-4344, 2001.

Eder, J.P. et al., "Recombinant Human Endostatin: Results of a Phase I Clinical Trial." Presented in Amsterdam, American Association of Cancer Research, Nov. 7, 2000.

\* cited by examiner

Detection of KDR-positive cells in human peripheral blood

| Sample | KDR-Positive cells / 1 ml |
|---|---|
| Control #1 | 3 |
| Control #2 | 4 |
| Control #3 | 9 |
| Patient #1 (1/8/01) | 364 |
| Patient #2 (1/16/01) | 313 |
| Patient #3 (1/18/01) | 248 |

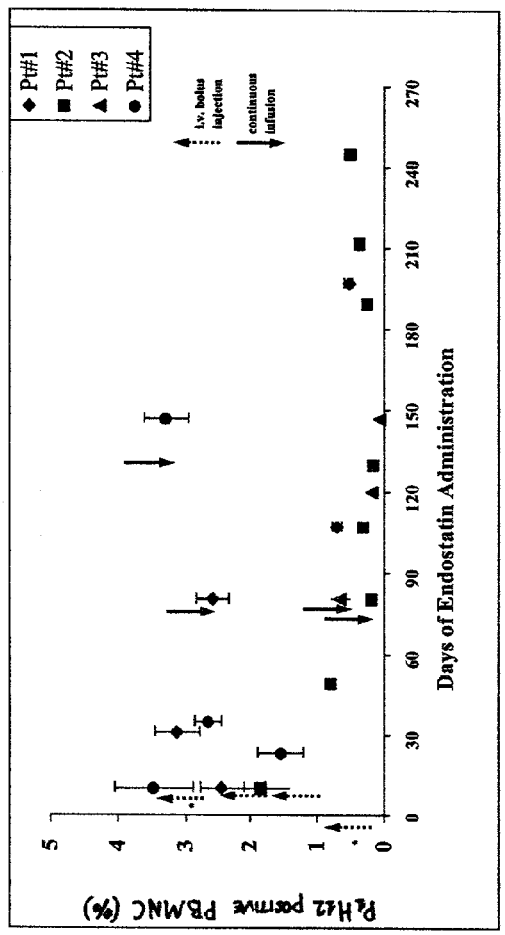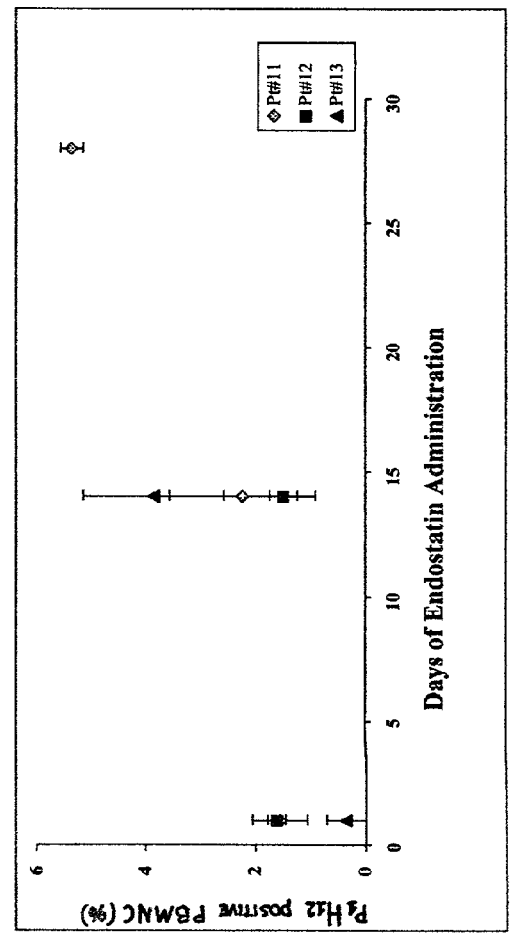
Figures 6A-B

METHODS FOR ASSESSING ANTIANGIOGENIC AGENTS

CROSS-REFERENCE TO RELATED APPLICATIONS

This application claims priority benefit of U.S. Provisional Application Ser. No. 60/290,390 filed on May 11, 2001 the content of which is relied upon and incorporated herein by reference in its entirety, and benefit priority under 35 U.S.C. §119(e).

FIELD OF THE INVENTION

The present invention relates to antiangiogenic therapy. Specifically, the present invention is directed to a method for screening and assessing antiangiogenic activity for therapeutic, diagnostic and prognostic applications.

BACKGROUND OF THE INVENTION

Formation of new blood vessels and capillaries (neovascularization) is comprised of two different processes: vasculogenesis, the in situ assembly of capillaries from undifferentiated endothelial cells (EC), and angiogenesis, the sprouting of capillaries from preexisting blood vessels. Vasculogenesis takes place mostly during the early stages of embryogenesis (Folkman and D'Amore, 1996; Yancopoulos et al., 1998). The vasculogenic process can be divided into five consecutive steps (Drake et al., 1998): (1) EC are generated from precursor cells, called angioblasts, in the bone marrow; (2) EC form the vessel primordia and aggregates that establish cell-to-cell contact but have no lumen; (3) a nascent endothelial tube is formed, composed of polarized EC; (4) a primary vascular network is formed from an array of nascent endothelial tubes; and (5) Pericytes and vascular smooth muscle cells are recruited to form the mature vessel.

In mammals, normal angiogenesis is confined to the reproductive system, embryogenesis and development, and repair after injury. Undesirable or pathological neovascularization has been associated with disease states including diabetic retinopathy, psoriasis, cancer, rheumatoid arthritis, atheroma, Kaposi's sarcoma and haemangioma (Fan et al, Trends Pharmacol. Sci. 16: 57-66 (1995); Folkman, Nature Medicine 1: 27-31 (1995)). Alteration of vascular permeability is thought to play a role in both normal and pathological physiological processes (Cullinan-Bove et al, Endocrinology 133: 829-837 (1993); Senger et al, Cancer and Metastasis Reviews. 12: 303-324 (1993)). Intraocular neovascularization is usually associated with diabetic retinopathy and retinopathy of prematurity (King and Brownlee, 1996). The new blood vessels are leaky and rupture easily, which may result in blindness. In chronic inflammatory diseases such as rheumatoid arthritis, new vessels invade the joint surfaces and degrade the cartilage by proteolysis (Battegay, 1995).

But most notably, a growing body of evidence indicates that angiogenesis is essential to the progression of cancer because it is a prerequisite for tumor growth and metastasis (Folkman, 1992). Without vascularization, tumors may remain for years as small (less than a few millimeters) asymptomatic lesions. Weidner et al. New England J. of Med. 324: 1-8 (1991). Tumors which become vascularized receive increased oxygen and nutrients through perfusion. Thus, tumors which are vascularized can grow and proliferate. A tumor must constantly stimulate the growth of new capillary blood vessels in order for it to continue to grow. Additionally, angiogenesis allows the tumor cells access to the host animal's circulatory system. The new blood vessels provide a gateway for tumor cells to enter the circulation and metastasize to distant sites. (Folkman, J. Natl. Cancer Inst. 82:4-6 (1990); Klagsbrunn and Soker, Current Biology 3:699-702 (1993); Folkman, J., J. Natl., Cancer Inst. 82:4-6 (1991); Weidner et al., New Engl. J. Med. 324:1-5 (1991)).

In fact, the extent of neovascularity is strongly correlated with metastases in primary breast carcinoma, bladder cancer, prostrate cancer, non-small cell lung cancer, cutaneous melanomas, and uterine cervix carcinoma. (Reviewed in Ferrara, N., Breast Cancer Research and Treatment 36: 127-137 (1995)). In these studies, tumor specimens were histologically analyzed and the number of microvesicles manually counted. The extent of tumor mass vascularization was found to be an independent predictor of the metastatic potential, and more reliable than other prognostic markers.

These results have led researchers to speculate that tumor vascularization could be used as a diagnostic tool to predict metastasis. However, counting of microvesicles in tumor specimens, besides being labor-intensive, is a qualitative art. The method requires considerable technical training in order to obtain reliable and reproducible results. Some groups have reported difficulties in reproducing the method. (Wiedner, N., Amer. J. Path. 147: 9-19 (1995)). Additionally, the process of preparing specimens for histology and counting vesicles is time consuming. Therefore, the application of this technique has been limited generally to research purposes.

Several investigators have theorized that one may be able to measure angiogenic activity in patients by quantitating the presence of angiogenic proteins. There are twelve known angiogenic proteins whose presence could potentially indicate angiogenesis. (Folkman J. New England J. of Med. 333: 1757-63 (1995)). Of these factors, those most commonly found to be associated with tumors are basic fibroblast growth factor (bFGF), vascular endothelial growth factor (VEGF), insulin growth factor-2, platelet derived growth factor, and colony stimulating factors. Other factors which are candidates for angiogenic and metastatic markers are urokinase-type plasminogen activator and plasminogen activator inhibitor-1, as well as a variety of collagenases and urokinases. (Wiedner, N., Amer. J. Path. 147: 9-19 (1995)).

Recent evidence indicates that VEGF is an important stimulator of both normal and pathological angiogenesis (Jakeman et al, Endocrinology, 133: 848-859 (1993); Kolch et al, Breast Cancer Research and Treatment, 36:139-155 (1995)) and vascular permeability (Connolly et al, J. Biol. Chem. 264: 20017-20024 (1989)). Antagonism of VEGF action by sequestration of VEGF with antibody can result in inhibition of tumor growth (Kim et al, 1993, Nature 362: 841-844). To this end, major progress has been made in the study of molecules that display antiangiogenic activity and may have therapeutic potential. Several naturally occurring antiangiogenic molecules, have been discovered, including: thrombospondin-1, platelet factor-4, fumagillin derivative AGM-1470 (TNP-470), thalidomide, angiostatin and endostatin (Folkman, 1995). These molecules can inhibit endothelial cell (EC) proliferation in vitro, disrupt endothelial tubes, and most importantly, repress tumor growth in vivo (O'Reilly et al., 1997; O'Reilly et al., 1994). Although antiangiogenic factors have attracted much attention, their mechanism of action is not yet clear.

Recent studies have also reported on the presence of circulating endothelial progenitor cells (EPC) in the bloodstream (Asahara et al., 1997; Shi et al., 1998). EPC can be recruited to distinct sites, and upon stimulation with angiogenic factors and cytokines, these cells can differentiate into mature EC and participate in the angiogenic process (Asahara et al., 1999; Takahashi et al., 1999). It has been shown that circulating EPC from human peripheral blood, could be isolated and grown in culture (Asahara et al., 1997). Culturing EPCs in the presence of VEGF enhanced their differentiation to mature EC and promoted the formation of endothelial tubes and subsequent expression of endothelial nitric oxide synthetase. In vivo treatment of mice with VEGF resulted in increasing numbers of circulating EPC (Asahara et al., 1999). Using the cornea micropocket assay, it was shown that VEGF also enhanced the incorporation of EPC into the growing capillaries in the eye.

There thus remains a need for a rapid and objective technique that could be used generally to screen and assess tumor angiogenesis and thus be used (a) to isolate new antiangiogenic agents, (b) to monitor the progress of an antiangiogenic treatment and thereby allow for a custom treatment protocol to be devised, and (c) as a prognostic/diagnostic indicator of angiogenic diseases.

SUMMARY OF THE INVENTION

The object of the present invention is to provide methods for screening and assessing antiangiogenic activity for therapeutic, diagnostic and prognostic applications directed to diseases involving abnormal angiogenesis.

In one embodiment, the present invention provides a method of assessing a therapeutic effect of an antiangiogenic agent in a patient being treated with the agent. The method comprises (a) measuring the level of endothelial progenitor cells at time point A; (b) administering the antiangiogenic agent; (c) measuring the level of endothelial progenitor cells at time point B; and (d) determining whether there is a change in the level of endothelial progenitor cells from the measurement at point A to the measurement at point B, wherein a decrease in the level of endothelial progenitor cells indicates that the antiangiogenic agent is producing the desired therapeutic effect. Preferably, the point A is before the patient undergoes antiangiogenic therapy, and the point B is seven days after the patient undergoes antiangiogenic therapy. Preferably, the level of the endothelial progenitor cells is determined by measuring the endothelial progenitor cells' surface markers.

In another embodiment of the present invention, there is provided an in vitro method of screening compounds for potential antiangiogenic activity. The method comprises (a) obtaining a blood sample; (b) purifying peripheral blood mononuclear cells (PBMNC) from the blood sample; (c) obtaining non adherent cells from the PBMNCs; (d) contacting the resulting non adherent PBMNC cells with an angiogenic agent for a period of time sufficient to effect cell growth; (e) measuring the resulting PBMNCs or PBMNC colonies; (f) subsequently contacting the culture medium with a test compound; and (g) measuring any resulting PBMNC colonies or their differentiation to adherent and elongated cells, wherein a decrease in the number of PBMNC colonies or their differentiation indicates that the test compound is potentially antiangiogenic. Preferably, the angiogenic agent is VEGF or bFGF, or both.

In yet another embodiment of the invention, there is provided a method of screening for compounds for potential antiangiogenic activity. The method comprises (a) administering an angiogenic agent into a host's blood circulation; (b) measuring a level of endothelial progenitor cells; and (c) subsequently delivering a test compound to the host and measuring the level of the endothelial progenitor cells, wherein a decrease in the level of endothelial progenitor cells indicates that the test compound is potentially antiangiogenic. In the method of screening compounds for potential antiangiogenic activity, endothelial cell specific markers are representative of endothelial progenitor cells. Preferably, the angiogenic agent is VEGF or bFGF. Both VEGF and bFGF may be used in combination.

In a further embodiment of the invention, there is provided a method of preventative diagnosis of an individual at risk for developing an angiogenic disease. The method comprises screening the individual for levels of endothelial progenitor cells (EPCs) above a baseline level obtained from a normal population. The angiogenic disease is, for example, cancer, such as breast cancer or ovarian cancer.

It is to be understood that while the invention has been described in conjunction with the preferred specific embodiments thereof that the foregoing description as well as the examples that follow are intended to illustrate and not limit the scope of the invention. Other aspects, advantages and modifications within the scope of the invention will be apparent to those skilled in the art to which the invention pertains. All publications, patent applications, patents and other references mentioned herein are incorporated by reference. In addition, the materials, methods and examples are illustrative only and not intended to be limiting. In case of conflict, the present specification, including definitions, controls.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention. In the drawings.

FIG. 3 shows the number of KDR-positive cells in blood samples from cancer patients and healthy volunteers.

FIGS. 6A-B illustrate the effect of endostatin treatment on the number of circulating EPC in cancer patiens with slow-progressing cancer (FIG. 6A) and faster-progressing cancer (FIG. 6B).

DESCRIPTION OF THE INVENTION

Figure 1:
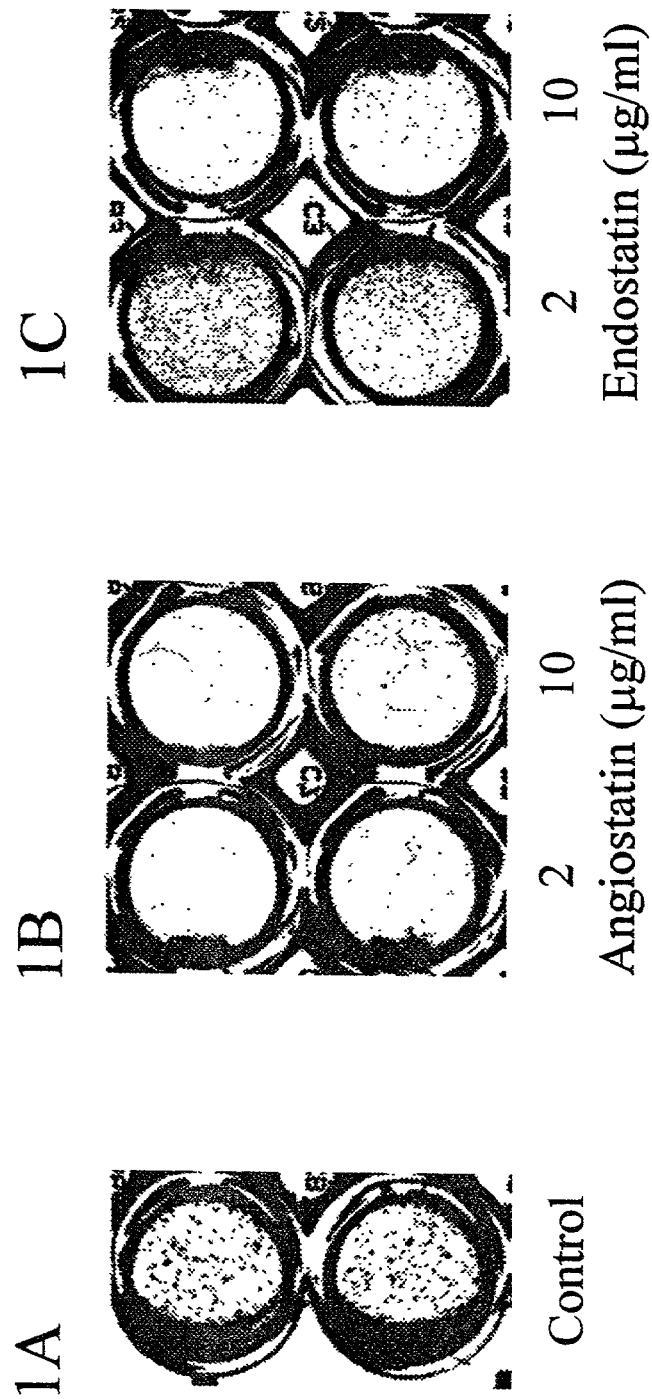
FIGS. 1A-C show human peripheral blood mononuclear cells stained with methyl-methylene blue and counted in the absence of antiangiogenic agents (FIG. 1A); in the presence of angiostatin (FIG. 1B); and in the presence of endostatin (FIG. 1C).

The present invention provides methods for utilizing endothelial progenitor cells (EPC) to isolate and test new antiangiogenic agents; for diagnostic applications including monitoring the progress of an antiangiogenic treatment and thereby maximizing the effect of the treatment by adjusting the dose and duration of the treatment; and for prognostic/diagnostic applications such as screening an individual at risk for developing an angiogenic disease, for example, cancer.

In a preferred embodiment of the invention, abnormal angiogenesis is monitored in a human subject by assaying the expression of specific molecular markers associated with EPCs. Any disease characterized by abnormal angiogenesis may be molecularly staged using the method of the invention, such as retinal neovascularization, neovascularization in atherosclerotic plaques, hemangiomas, arthritis, psoriasis, cancer, and tumor metastasis. The information acquired through this diagnostic tool is used by the physician to design treatment protocols for which to treat and manage the disease condition. For example, high levels of EPCs indicate that the disease has an increased angiogenic capacity and thus may be best treated with antiangiogenic agents. Conversely, low levels of EPCs would direct the physician to use standard chemotherapeutic treatment.

In one aspect of the invention, the level of circulating EPCs, based on their cell surface specific markers, is detected and monitored before, during and after the administration of an antiangiogenic agent to a patient with abnormal angiogenesis. EPC specific markers include molecules that are expressed in EPCs as well as molecules that are expressed in ECs and are indicative of the presence of EPCs. Suitable markers include but are not limited to KDR/flk-1, CD133, flt-1, neuropilin and/or tek/tie-2 receptor proteins. Because an abnormally increased level of EPCs relates to the onset of increased angiogenesis, the level of EPC is a molecular marker for the angiogenic capacity of the disease. Thus, an increased level of EPCs prior to any treatment is indicative that the disease will be responsive to an antiangiogenic agent. Whereas, a decrease in the level of EPCs due to an antiangiogenic treatment indicates that the agent is having its desired effect. And, an unchanged level in the amount of a marker during the course of administration of an antiangiogenic agent may be indicative of an ineffective dose of the agent. The presence of EPCs may be assayed in blood obtained through any method known in the art.

Another aspect of the present invention is a method of preventative diagnosis of an individual at risk for developing an angiogenic disease. The method involves screening an individual for levels of EPC above a baseline level obtained from a normal population.

A further aspect of the invention is a method of screening for new antiangiogenic compounds. The screening method of the present invention can be performed in vitro and in vivo. The in vivo method monitors the production EPCs, whereas the in vitro method monitors the differentiation of EPCs to ECs.

The in vitro method involves obtaining a blood sample, purifying peripheral blood mononuclear cells (PBMNC), treating the PBMNCs to obtain non adherent cells, contacting the non adherent PBMNCs with a medium comprising an angiogenic agent, e.g., VEGF or bFGF, or both, for a period of time sufficient to affect cell growth, subsequently administering to the culture medium a test compound, culturing the cells for a time sufficient to determine the effect of the test compound, and counting the number of resulting colonies and/or their differentiation to adherent and elongated cells. Effective antiangiogenic compounds, in contrast to a control compound such as TNP-470, interfere with the formation of PBMNC colonies as well as block the differentiation of these cells to adherent and elongated cells, which are the EPCs. If, on the other hand, the test compounds are not antiangiogenic, large number of colonies containing elongated cells result.

The in vivo method of screening for new antiangiogenic compounds involves delivering angiogenic agents, such as VEGF or bFGF, into an experimental animal's circulation to produce an increased number of EPCs, measuring the level of EPCs, or, for example, by measuring specific markers, subsequently delivering the test compound and measuring the level of resulting circulating EPCs. A decrease in the number of EPCs in the animal's blood circulation is an indicator that the test compound is potentially an antiangiogenic agent.

Additionally, the methods recited above may be used in high throughput screens for antiangiogenic agents.

Accordingly, we have discovered that endothelial progenitor cells (EPC) are particularly suitable for use in a sensitive assay for antiangiogenic factors. We have found that EPC mobilization and differentiation is greatly inhibited by antiangiogenic factors as evidenced in vivo by VEGF inducing a massive mobilization of EPC into the blood circulation which effect is significantly inhibited by endostatin treatment, and, in vitro, human blood-derived EPC forming adherent colonies, which colonies, in the presence of angiogenic factors, give rise to differentiated EC, and which differentiation is disrupted and cell growth is inhibited in the presence of angiostatin and endostatin.

Identification of new antiangiogenic factors has allowed the use of some of these factors for experimental treatment of cancer, atherosclerosis and retinopathy (Folkman, 1996). However, before being used pharmacologically, the total effect of each factor alone or in combination with others must be realized.

We have invented a method of testing the effects of antiangiogenic factors on EPC using in vitro and in vivo systems. The results from the in vitro assay indicate that angiostatin and endostatin significantly inhibit the formation of adherent colonies of cells from human and mouse peripheral blood. These results indicate that angiostatin and endostatin might interfere with VEGF and bFGF-mediated differentiation of EC from their progenitors. The amounts required to achieve these effects are comparable or lower than the amount required to inhibit bFGF-induced EC proliferation (O'Reilly et al., 1997; O'Reilly et al., 1994). However, we found that the effect of angiostatin in the EPC in vitro differentiation assay is more pronounced than its effect on EC proliferation. Cumulatively, EPC in vitro differentiation assay is a sensitive method to test antiangiogenic activity of newly discovered factors.

We have also tested the effects of endostatin on EPC in vivo in mice. The percentage of EPC, based on their cell surface markers (Flk-1, CD34 and AC133), in humans is very low (0.2% of total PBMNC) and only 3% of EPC can adhere and give rise to mature EC in vitro (Shi et al., 1998). In mice, the proportion of EPC is similar to humans' but the amount of blood available from each individual mouse is limited thus, making the analysis of EPC in mice difficult. Only upon delivery of VEGF into the mouse circulation, a large number of EPC-containing colonies were detected. Many of the cells within these colonies had an elongated shape and they expressed endothelial specific markers. Endostatin treatment results in complete inhibition of VEGF-induced PBMNC colony formation. Therefore, the levels of circulating EPC appear to serve to indicate endostatin potency. Moreover, since EPC are suspected to have an important role in neovascularization (Asahara et al., 1999), the antiangiogenic effect of endostatin may be explained in part by the suppression of EPC presence in the blood.

Various assays can be designed to measure angiogenic and antiangiogenic potential. The in vitro EC proliferation or migration assays can demonstrate if a factor can act directly on EC, but can not predict the extent of the in vivo effect. The simplest in vivo assay to measure antiangiogenesis is performed in the chorioallantoic membrane (CAM) (Nguyen et al., 1994). Angiogenic factors such as VEGF and BFGF induce the formation of a heavy capillary network on the CAM, whereas TNP-470, angiostatin and endostatin greatly inhibit CAM vascularization. Other assays are currently used to test the potential of angiogenic and antiangiogenic factors in vivo. The cornea micropocket assay is performed by inserting the factor into a small incision in the cornea of a rat or a mouse (Kenyon et al., 1996). New blood vessels growing into the avascular cornea are then analyzed. The antiangiogenic factor can be injected intravenously in order to assay its systemic effect. Our data shows that circulating EPC and their differentiation to mature EC may serve as a sensitive assay to measure the potential on antiangiogenic factors. This assay may be performed in vitro and in vivo and may be used to screen large numbers of compounds for their possible angiogenic and antiangiogenic activity.

In summary, we have shown that antiangiogenic agents such as angiostatin and endostatin can interfere with mobilization and differentiation of EPC, by using an in vitro and in vivo assay systems. In addition, these results suggest a possible mechanism of action for angiostatin and endostatin, two of the most potent antiangiogenic factors isolated so far (O'Reilly et al., 1997; O'Reilly et al., 1994).

The invention will be further clarified by the following examples which are intended to be exemplary of the invention.

EXAMPLES

Angiostatin and Endostatin Inhibit In Vitro Formation of Colonies from Human Peripheral Blood Human peripheral blood mononuclear cells (PBMNC) were purified over Ficoll gradient and seeded onto non-treated plastic dish for 24 hr. Non. adherent cells were, transferred to a gelatin coated 48 well dish in medium containing basic fibroblast growth factor (BFGF) and VEGF. Angiostatin and endostatin were added to the medium 24 hours later and cells were cultured for additional 6 days. At the end of the experiment the colonies were fixed with ethanol, stained with methyl-methylene blue and counted (FIGS. 1A-C). In the absence of antiangiogenic factors (FIG. 1A), large number of colonies containing elongated cells were formed. Angiostatin at 2 and 10 μg/ml completely blocked the formation of PBMNC colonies and only small aggregates of round cells were observed (FIG. 1B). There was no difference in the effects of angiostatin between the two concentrations used. Endostatin, on the other hand, showed different effects at 2 and 10 μg/ml (FIG. 1C). At the lower concentration, the number of colonies grew but the colonies were small and contained small round cells. At 10 μg /ml endostatin, the number of PBMNC colonies was significantly lower than the control experiment. These results indicate that antiangiogenic factors such as angiostatin and endostatin interfere with the formation of PBMNC colonies as well as with the differentiation of these cells to adherent and elongated cells, which are probably the precursors of EC. Taken together, it appears that angiostatin and endostatin block the differentiation of EC from their circulating progenitors.

Endostatin Suppress VEGF-Induced Mobilization of EPC in Mice

Figure 2:
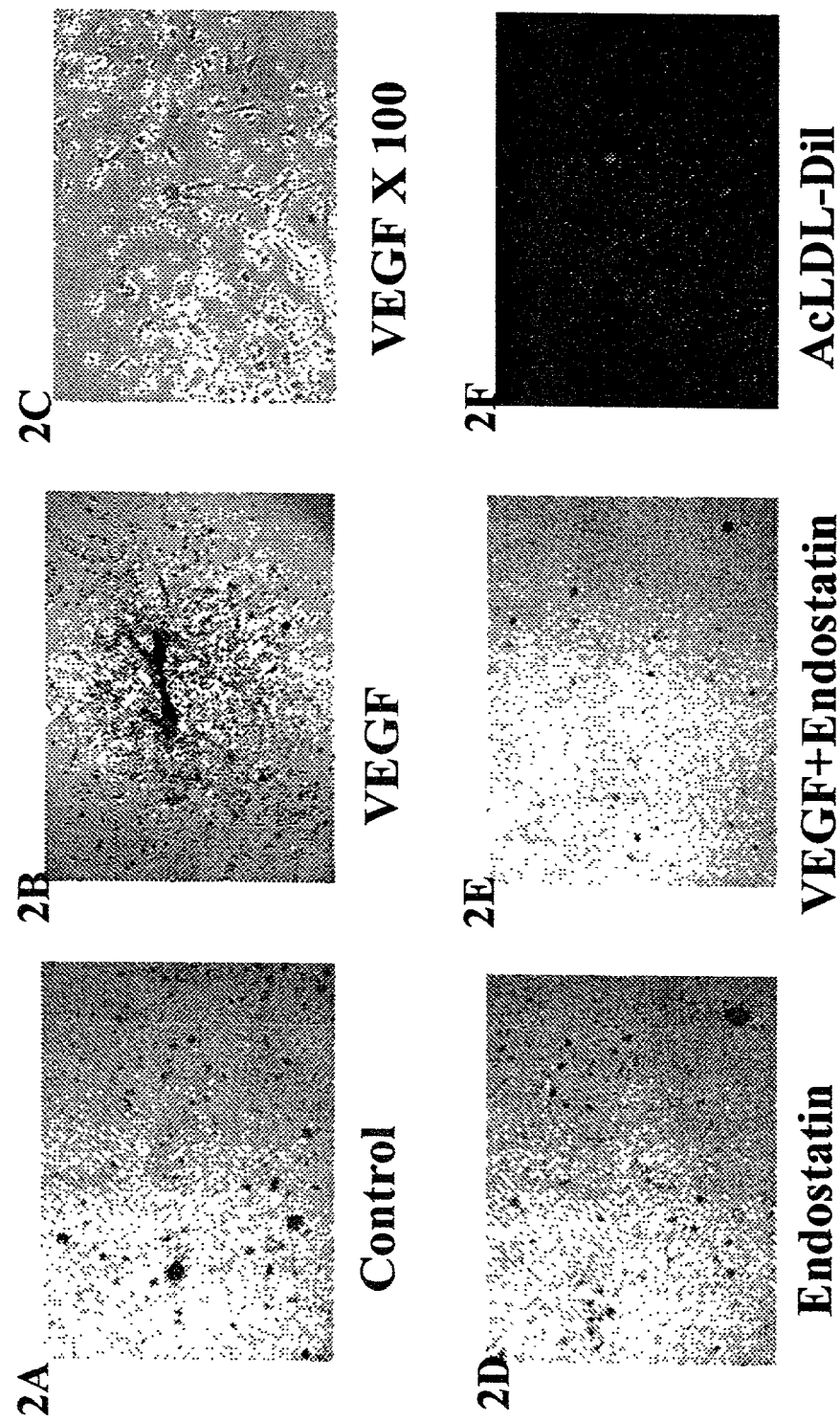
FIGS. 2A-F depict mononuclear cells from peripheral blood plated in medium containing angiogenic and antiangiogenic agents: VEGF (FIGS. 2B and 2C); Endostatin (FIG. 2D); VEGF with Endostatin (FIG. 2E); and VEGF with dil-labeled ac-LDL (FIG. 2F).

The number of circulating EPC in healthy human and mice is very low (about $2 \times 10^{-3}$ of total PBMNC) and most of them do not readily adhere. PBMNC from 1 ml of peripheral mouse blood were plated in medium containing bFGF and VEGF (FIG. 2A). After 7 days in culture no viable cell-containing colonies could be detected. Similar results were obtained with peripheral blood from mice, which were injected with microencapsulated cells producing endostatin (approximately $0.5 \times 10^6$ cells per mice) (Joki et al., 2001) (FIG. 2D).

In order to elevate the number of EPC in the blood, the mice received injection of $0.5 \times 10^6$ cells producing VEGF, that were micro-encapsulated similar to the endostatin producing cells (FIGS. 2B-C). Large number of colonies was obtained from peripheral blood of these mice and the colonies consisted of many adherent and elongated cells that incorporated dil-labeled ac-LDL into their membrane (FIG. 2F). In contrast, when mice received VEGF producing cells together with endostatin producing cells ($0.5 \times 10^6$ alginate encapsulated cells of each), only a few, small and round cell-containing colonies were detected (FIG. 2E). Hence, VEGF treatment is useful for elevating the number of EPC in peripheral blood in contrast to endostatin treatment which resulted in a significant reduction in the number of EPC containing colonies.

PBMNC from VEGF injected mice were further analyzed by immunostaining in order to confirm their identity. Blood-derived cells were stained positively for VEGF-R2 (Flk-1), CD-31, BS-1 (a lectin specifically expressed on mouse EC) and for von-Wilerband factor (F.VIII). Only a few cells were stained positively for CD-14, a marker for macrophages. This result indicates that many of the cells within the colonies, derived from VEGF treated mice, express EC specific markers and probably represent EPC. Taken together, these results suggest that differentiation and mobilization of EPC are significantly suppressed by endostatin. Furthermore, this in vivo effect of endostatin can be seen only if the starting number of EPC in the blood is high as a result of the VEGF treatment.

Identification of EPC in Peripheral Blood of Cancer Patients

High levels of VEGF are produced by many human tumors and elevated levels of circulating VEGF have been found in cancer patients. Since our data indicate that high levels of VEGF can induce mobilization and differentiation of EPC, we have analyzed blood samples from cancer patients and healthy volunteers for the presence of EPC. MNC were purified from 1 ml peripheral blood using Ficoll gradient and placed in a "Cytospin" tube. The cells were pelleted onto glass slides, fixed and immunostained with anti-KDR antibodies, that were further detected by FITC-labeled (green) secondary antibodies. Cell nuclei were stained with DAPI (blue). Under light microscopy, many round cells were observed and their nuclei were stained blue using fluorescence microscopy. In addition, a few green-labeled cells were observed under fluorescence microscopy. These cells express KDR and they probably represent circulating EPC. Using this technique, the number of KDR-positive cells in blood samples from cancer patients and healthy volunteers was determined (FIG. 3). In the healthy volunteer group the number of KDR-positive cells ranged from 3 to 9 per 1 ml peripheral blood, whereas in cancer patient the number was much higher, between 248 to 364 per 1 ml peripheral blood. These results are similar to the results of our murine model of VEGF-induced mobilization and differentiation of EPC and suggest that the high numbers of EPC in peripheral blood of cancer patients might indicate their increased angiogenic capacity. Thus, analysis of circulating EPC might be useful for "angiogenic grading" of cancer patients. Moreover, the significant decrease of circulating EPC numbers after treatment with endostatin suggests that patients with high angiogenic grade might benefit more from anti-angiogenic therapy using endostatin and angiostatin.

Endostatin Inhibits Tumor-Induced Mobilization of EPC

Many tumors secrete high levels of VEGF that can promote differentiation and mobilization of EPC. To test the effects of endostatin on tumor-induced mobilization of EPC, SCID mice (5 per group) were first injected subcutaneously with human pancreatic tumor cells (HS-VF cell, $2 \times 10^6$ cells/mouse) overexpressing VEGF. Eight days later half of the mice were implanted with "Alzet" osmotic pumps releasing murine endostatin (8-12 mg/kg/day) and the other half with pumps releasing saline. SCID mice that were not injected with tumor cells or pumps (normal SCID mice) served as a control to measure the number of EPC. After seven days, mice were sacrificed and blood samples were collected.

Figure 4A:
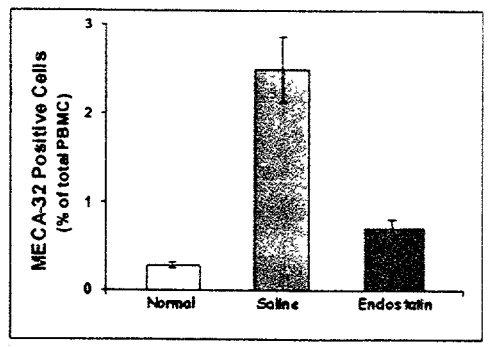
FIGS. 4A-C illustrate that endostatin inhibits tumor-induced mobilization of EPC in mice, as tested in PBMNC (FIGS. 4A) and in whole blood (FIGS. 4B-C).

PBMNC were purified over "Ficoll" gradient and cells corresponding to 0.5 ml of blood were placed in a "Cytospin" tube. The cells were loaded onto glass slides, fixed and immunostained with MECA-32 antibodies, that specifically detect murine EC. The staining was developed with FITC-labeled (green) secondary antibodies and cell nuclei were stained with DAPI (blue). The proportion of MECA-32 positive cells from total PBMNC was calculated and shown in the graph of FIG. 4A.

Figure 4B:
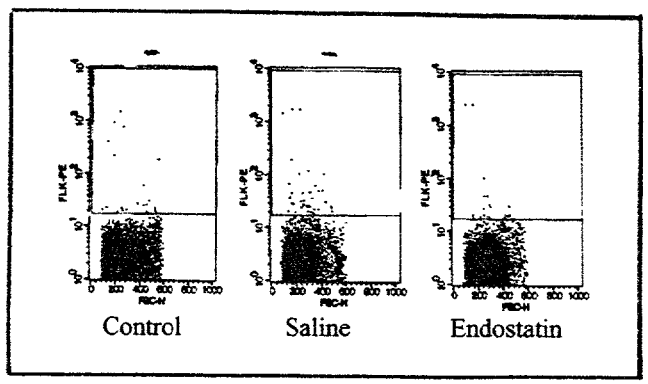
Figure 4C:
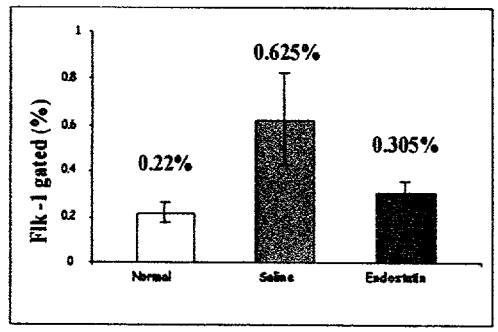

Control mice had 0.29% MECA-32 positive cells in the PBMNC preparation. The proportion of MECA-32 positive cells was approximately ten fold-higher in mice injected with tumor cells and implanted with pumps releasing saline, reaching approximately 2.5%. In contrast, mice implanted with pumps releasing endostatin had a significantly lower proportion of MECA-32 positive cells, 0.67%. These results were confirmed by fluorescent activated cell sorting (FACS), using phycoerythrin (PE) conjugated anti-Flk-1 antibodies (FIG. 4B). Normal mice had 0.22+/−0.04% gated Flk-1 positive cells among PBMNC. Blood samples from mice injected with tumor cells and implanted with pumps releasing saline had a significant higher number of Flk-1 positive cells reaching 0.625+/−0.19% gated cells. In contrast, tumor-bearing mice implanted with pumps releasing endostatin had 0.305+/−0.05% gated Flk-1 positive cells in the peripheral blood. Although the average number of Flk-1 positive cells in endostatin treated mice was higher than in normal mice, there was no significant difference between the two groups. In order to rule out possible cytotoxic effects of endostatin on the tumor cells, proliferation assays were performed in the presence or absence of 1 µg/ml endostatin.

Figure 5A:
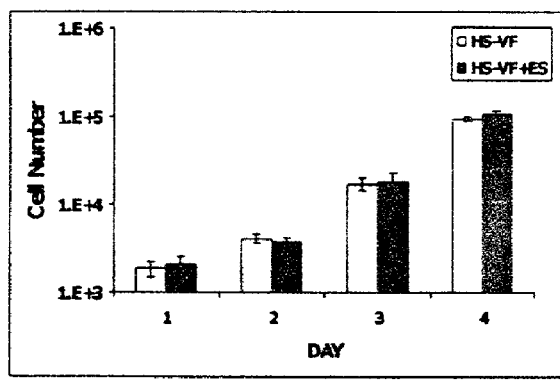
FIGS. 5A-B illustrate that endostatin has no significant effect on HS-VF cell proliferation (FIG. 5A) and VEGF expression in vivo (FIG. 5B).
Figure 5B:
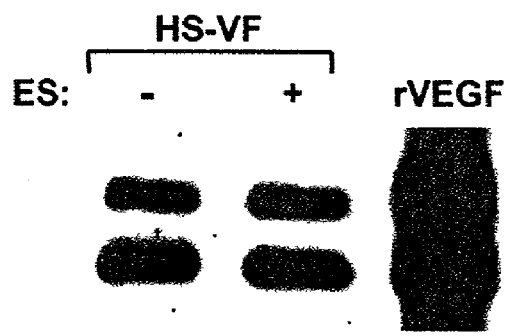

There was no effect of endostatin on the proliferation rate of the tumor cells, as shown in FIG. 5A, wherein HS-VF cells seeded in a 48 well dish ($1 \times 10^3$ cells per well) were grown in the presence (black bars) or absence (white bars) of 1 µg/ml of recombinant human endostatin. Cell number was determined every 24 hours for 4 days. Moreover, the amounts of VEGF in the conditioned media were similar for control cells and cells treated with endostatin, as shown in FIG. 5B. Conditioned medium was removed from cells cultured for 4 days in the presence (+) or absence (−) of endostatin. VEGF was purified using heparin Sepharose chromatography and detected by Western blot analysis. Recombinant $VEGF_{165}$ (rVEGF) was resuspended in culture media and purified using the same method. Taken together, these results indicate that endostatin significantly reduced the number of tumor-induced EPC without affecting the tumor cells directly.

EPC in Peripheral Blood of Cancer Patients Undergoing Endostatin Treatment

Recombinant human Endostatin (rhEndostatin, Endostatin™ EntreMed, Inc, Rockville, Md.) is under investigation in clinical Phase I trials in patients with advanced, refractory cancers. Twenty eight patients, age ranging from 28 to 72 years old with various types of cancer such as breast, colorectal and soft tissue sarcoma, participated in a phase I clinical trial at the Dana Farber Cancer Institute in Boston. We obtained blood samples from 7 patients that were treated with endostatin. The response of EPC to rhEndostatin differed between patients in accordance with differing clinical courses. The first group consisted of 4 patients with slowly progressive, stable or decreasing cancers that were followed with samples for 130-250 days (FIG. 6A). The second group consisted of patients with faster progressing cancer unaffected by rhEndostatin administration. This group was followed during 30 days of endostatin treatment (FIG. 6B). PBMNC were purified from the blood over "Ficoll" gradient and cells corresponding to 0.5 or 1 ml of blood were placed in a "Cytospin" tube. The cells were loaded onto glass slides, fixed and immuno-stained with FITC-conjugated P1H12 antibodies. Cell nuclei were stained with DAPI. The number of P1H12-positive cells was calculated as percentage of total PBMNC. EPC percentage varied among patients and was between 1.8-3.5%. These numbers are significantly higher than the values reported for healthy volunteers (approximately 0.2%). Patients from the first group were initially administered with daily intravenous injections of 60 mg/m$^3$ endostatin. The number of EPC was gradually decreased in two patients (#2 and #3). The administration of endostatin was later changed to continuous infusion (60 mg/m$^3$/day). In three of the patients (#1, #2 and #3) the number of EPC was further lowered by the continuous infusion and in one patient the number was not increased for 130 days.

The second group of patients were at the beginning of endostatin treatment (daily IVB injections of about to 240 mg/m$^3$). The initial amount of EPC in this group varied between 0.4-1.6%. In one patient EPC percentage did not change significantly during the first 15 days of endostatin administration (#12). In the other two patients the percentage of EPC increased significantly from 1.6 to 5.3% during 30 days of endostatin administration (#11) and from 0.4 to 3.8% during 15 days of endostatin administration (13). In these patients only 2-3 measurements of EPC were available because of rapid disease progression. Taken together, these results indicate that cancer patients have a higher number of EPC, confirming the results of the experiments in mice. On the other hand, minor response or stable disease progression upon endostatin administration was associated with reduction in the number EPC in peripheral blood, whereas an increase in EPC was associated with rapid disease progression. These results suggest that changes in the number of EPC may reflect the response of each patient to endostatin and thus, EPC number may be used as a surrogate marker for determining effectiveness of the endostatin and other antiangiogenic treatment.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The references cited below and incorporated throughout the application are incorporated herein by reference.

REFERENCES

1. Asahara, T., Masuda, H., Takahashi, T., Kalka, C., Pastore, C., Silver, M., Keame, M., Magner, M., and Isner, J. M. (1999). Bone marrow origin of endothelial progenitor cells responsible for postnatal vasculogenesis i-n physiological and pathological neovascularization. Circ Res 85, 221-8.
2. Asahara, T., Murohara, T., Sullivan, A., Silver, M., van-der-Zee, R., Li, T., Witzenbichler, B., Schatteman, G., and Isner, J. M. (1997). Isolation of putative progenitor endothelial cells for angiogenesis. Science 275, 964-967.

3. Asahara, T., Takahashi, T., Masuda, H., Kalka, C., Chen, D., Iwaguro, H., Inai, Y., Silver, M., and Isner, J. M. (1999). VEGF contributes to postnatal neovascularization by mobilizing bone marrow-derived endothelial progenitor cells. EMBO J 18, 3964-72.
4. Battegay, E. J. (1995). Angiogenesis: mechanic insights, neovascular diseases, and therapeutic prospects. J Mol Med 73, 333-46.
5. Breier, G., Albrecht, U., Sterrer, S., and Risau, W. (1992). Expression of vascular endothelial growth factor during embryonic angiogenesis and endothelial cell differentiation. Development 114, 521-32.
6. Drake, C. J., Hungerford, J. E., and Little, C. D. (1998). Morphogenesis of the first blood vessels. Ann NY Acad Sci 857,155-79.
7. Folkman, J. (1995). Angiogenesis inhibitors generated by tumors. Mol Med 1, 120-2.
8. Folkman J. (1996). Fighting cancer by attacking its blood supply. Scientific American 275,150-4.
9. Folkman, J. (1992). The role of angiogenesis in tumor growth. Semin Cancer Biol 3, 6571.
10. Folkman, J., and D'Amore, P. A. (1996). Blood vessel formation: what is its molecular basis? Cell87, 1153-5.
11. Frank, S., Hubner, G., Breier, G., Longaker, M. T., Greenhalgh, D. G., and Werner, S. (1995). Regulation of vascular endothelial growth factor expression in cultured keratinocytes. Implications for normal and impaired wound healing. J Biol Chem 270, 12607-13.
12. Joki, T., Machluf, M., Atala, A., Zhu, J., Seyfried, N. T., Dunn, I. F., Abe, T., Black, P. M., and Carroll, R. S. (2001). Continuous release of endostatin from microencapsulated engineered cells for tumor therapy. Nat Biotechnol 19, 35-39.
13. Kenyon, B. M., Voest, E. E., Chen, C. C., Flynn, E., Folkman, J., and D'Amato, R. J. (1996). A model of angiogenesis in the mouse comea. Invest Ophthalmol Vis Sci 37, 1625-32.
14. King, G. L., and Brownlee, M. (1996). The cellular and molecular mechanisms of diabetic complications. Endocrinol Metab Clin North Am 25, 255-270.
15. Nguyen, M., Shing, Y., and Folkman, J. (1994). Quantitation of angiogenesis and antiangiogenesis in the chick embryo chorioallantoic membrane. Microvasc Res 47,3140.
16. O'Reilly, M. S., Boehm, T., Shing, Y., Fukai, N., Vasios, G., Lane, W. S., Flynn, E., Birkhead, J. R., Olsen, B. R., and Folkman, J. (1997). Endostatin: an endogenous inhibitor of angiogenesis and tumor growth. Cell 88, 277-85.
17. O'Reilly, M. S., Holmgren, L., Shing, Y., Chen, C., Rosenthal, R. A., Moses, M., Lane, W. S., Cao, Y., Sage, E. H., and Folkman, J. (1994). Angiostatin: a novel angiogenesis inhibitor that mediates the suppression of metastases by a Lewis lung carcinoma. Cell 79, 315-28.
18. Rivard, A., and Isner, J. M. (1998). Angiogenesis and vasculogenesis in treatment of cardiovascular disease. Mol Med 4, 429-40.
19. Shi, Q., Rafii, S., Wu, M. H., Wijelath, E. S., Yu, C., Ishida, A., Fujita, Y., Kothari, S., Mohle, R., Sauvage, L. R., Moore, M. A., Storb, R. F., and Hanunond, W. P. (1998). Evidence for circulating bone marrow-derived endothelial cells. Blood 92, 362-7.
20. Shweiki, D., Itin, A., Neufeld, G., Gitay-Goren, H., and Keshet, E. (1993). Patterns of expression of vascular endothelial growth factor (VEGF) and VEGF receptors in mice suggest a role in horrnonally regulated angiogenesis. J Clin Invest 91, 2235-43.
21. Takahashi, T., Kalka, C., Masuda, H., Chen, D., Silver, M., Kearney, M., Magner, M., Isner, J. M., and Asahara, T. (1999). Ischernia- and cytokine-induced mobilization of bone marrow-derived endothelial progenitor cells for neovascularization. Nat Med 5, 434-8.
22. Yancopoulos, G. D., Klagsbrun, M., and Folkman, J. (1998). Vasculogenesis, angiogenesis, and growth factors: ephrins enter the fray at the border. Cell 93, 661-4.

What is claimed is:

1. A method of assessing a therapeutic effect of an antiangiogenic agent in a patient having a disease associated with increased angiogenesis being treated with the agent comprising:
   a. measuring the level of endothelial progenitor cells in the blood of the patient at time point A;
   b. administering the antiangiogenic agent to the patient;
   c. measuring the level of endothelial progenitor cells in the blood of the patient at time point B; and
   d. determining whether there is a change in the level of endothelial progenitor cells in the blood of the patient from the measurement at point A to the measurement at point B, wherein a decrease in the level of endothelial progenitor cells in the blood of the patient indicates that the antiangiogenic agent is producing the desired therapeutic effect.

2. The method of claim 1, wherein the point A is before the patient undergoes antiangiogenic therapy.

3. The method of claim 1, wherein the point B is seven days after the patient undergoes antiangiogenic therapy.

4. The method of claim 1, wherein the level of the endothelial progenitor cells is determined by measuring the endothelial progenitor cells' surface markers.

5. The method of claim 1 wherein administering step b) results in decreased mobilization of endothelial progenitor cells from the patient's bone marrow into the patient's circulation.

6. The method of claim 1, wherein measuring of step a) and b) is by counting of EPC obtained from peripheral blood.

7. The method of claim 6, wherein counting is by identification of immunostained EPC.

8. The method of claim 6, wherein counting is by fluorescent activated cell sorting.

* * * * *

UNITED STATES PATENT AND TRADEMARK OFFICE
CERTIFICATE OF CORRECTION

PATENT NO.      : 7,666,393 B2                      Page 1 of 1
APPLICATION NO. : 10/142165
DATED           : February 23, 2010
INVENTOR(S)     : Soker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 278 days.

Signed and Sealed this

Twenty-eighth Day of December, 2010

David J. Kappos
*Director of the United States Patent and Trademark Office*